United States Patent [19]

Tsoucalas et al.

[11] 4,051,159

[45] Sept. 27, 1977

[54] TRANSPARENT FRAGRANCE RELEASING COMPOSITION AND METHOD OF MAKING SAME

[75] Inventors: Michael Tsoucalas, Bergenfield; Kenneth W. Barclay, Mahwah; Jack M. Rogers, Fairlawn, all of N.J.

[73] Assignee: Avon Products, Inc., New York, N.Y.

[21] Appl. No.: 648,204

[22] Filed: Jan. 12, 1976

[51] Int. Cl.$^2$ .................. C09F 5/00; A24F 25/00; A61K 7/46
[52] U.S. Cl. ..................... 260/404.5; 260/18 N; 252/522; 239/34; 239/54; 239/56; 239/60
[58] Field of Search .................. 260/404.5, 18 N; 252/522; 239/34, 35, 56, 60, 54

[56] References Cited

U.S. PATENT DOCUMENTS

| | | | |
|---|---|---|---|
| 2,169,055 | 8/1939 | Overshiner | 239/54 |
| 3,655,129 | 4/1972 | Seiner | 239/60 |
| 3,685,734 | 8/1972 | Paciorek et al. | 239/56 |
| 3,688,985 | 9/1972 | Engel | 252/522 |
| 3,772,215 | 11/1973 | Gould | 252/522 |
| 3,914,187 | 10/1975 | Fein et al. | 239/54 |
| 3,945,950 | 3/1976 | Vosganiantz | 239/60 |

Primary Examiner—Winston A. Douglas
Assistant Examiner—John F. Niebling
Attorney, Agent, or Firm—Pennie & Edmonds

[57] ABSTRACT

Shaped, self-supporting transparent fragrance emitting articles comprising a high percentage of a thermoplastic polyamide resin having substantially uniformly dispersed therein a $C_{14}$–$C_{22}$ alkyl alcohol and a fragrance emitting material, and the method of making such articles.

16 Claims, No Drawings

TRANSPARENT FRAGRANCE RELEASING COMPOSITION AND METHOD OF MAKING SAME

BACKGROUND OF THE INVENTION

Compositions which are intended to emit a fragrance over an extended period of time are well known. These include inert powdery carriers impregnated with essential oils as well as wax pomanders. They have been and are normally used as garment sachets, room air-fresheners and the like.

Polymeric materials have been substituted in whole, or in part, for wax as a carrier for fragrance emitting pomanders. U.S. Pat. No. 2,169,055 discloses a mixture of essential oils in cellulose acetate to form a fragrance emitting film or sheets and U.S. Pat. No. 3,655,129 discloses compositions comprising minute droplets of a liquid non-solvent containing fragrance oil which is dispersed in a polymeric matrix.

All of the foregoing pomander compositions are, however, not transparent, nor are they readily formed into molded articles which resist deformation, chipping and abrasion.

SUMMARY OF THE INVENTION

The present invention is directed to fragrance emitting self-supporting articles formed from compositions which permit retention of volatile fragrances therein while processing. The resultant articles are abrasion resistant, transparent, hard and uniquely suitable as a garment sachet, air freshener and the like.

Briefly, the present invention comprises shaped, self-supporting transparent articles capable of emitting fragrance over a sustained period comprising from about 40 to 60% by weight of a polyamide resin formed from a polymerized fatty carboxylic acid and a polyamine, from about 35 to 55% by weight of a $C_{14}$–$C_{22}$ alkyl alcohol and from about 5 to 20% by weight of volatile essential oil. The invention also comprises the hereinafter described method of making such articles.

DETAILED DESCRIPTION OF THE INVENTION

The polyamide resins useful in the present composition are long chain substantially linear amide resins derived from the reaction of a polymerized fatty acid with a di- or polyamine. Polymerizable fatty acids include $C_{16}$–$C_{22}$ linear acids having one or more than one unsaturated double bond in the hydrocarbon chain. Such compounds include palmitoleic, oleic, ricinoleic, vaccenic, linoleic, linolenic, eleostearic, punicic, gadoleic, cetoleic, erucic, and the like. Polyamides formed from $C_{18}$ fatty acids, such as, linoleic and oleic, are preferred with linoleic acid most preferred.

Suitable polyamines are aliphatic primary and secondary amines containing two or more amino groups therein. Polyamines which produce useful polyamide resins with the polymerized fatty acids described above may be, for example, alkylene diamine, such as, ethylene diamine, propylene diamine, tetramethylene diamine, hexamethylene diamine, and the like; dialkylene triamine, such as diethylene triamine, dipropylene triamine, and the like. Higher polyamines, such as triethylene tetraamine, tetraethylene pentaamine, may also be used. The polyamines may be used singly or in combination in conventional manner to form the desired polyamide resins.

The polyamides found useful in formulating the compositions of the instant invention have average molecular weight ranging from about 2,000 to 10,000 with from about 6,000 to 9,000 being preferred. They are formed by the condensation reaction of a polymerized fatty acid, normally as the dimer or trimer, with the polyamine. The preferred polyamides are formed from dimeric or trimeric linoleic acid and a polyamine. Such products are commercially available under the tradename "Versalon" of General Mills, Inc. including Versalon 1109, Versalon 1300, Versalon 1135, Versalon 1138, Versalon 1140, Versalon 1164, Versalon 1200 and the like with Versalon 1109, 1138 and 1164 being preferred. Polyamides having softening points of less than about 200° C (Ball & Ring) and preferably less than about 175° C and viscosity (Brookfield) of less than about 90 poises when measured at 225° C are preferred.

The polyamides described hereinabove have unexpectedly been found, when mixed with the alkyl alcohols described hereinbelow, to form a sufficiently fluid mass at the low processing temperatures presently used to permit substantial homogeneous mixing of the components and retention of the fragrance material therein yet to form a solid, self-supporting, transparent article which is resistant to flaking, chipping and abrasion at ordinary temperatures.

The polyamide resin described above must be used in combination with a $C_{14}$–$C_{22}$ alkyl alcohol. The alcohol may be a straight chain $C_{14}$–$C_{22}$ alkyl alcohol such as tetradecanol, pentadecanol, hexadecanol, octadecanol, eicosanol, docosanol, and the like, or a branched chain alcohol, such as 2-alkyl alkanols, 4-alkyl alkanols, 6-alkyl akanols, and the like having, combined, from 14 to 22 carbon atoms. Examples illustrating such compounds are 2-ethyl, 2-butyl, 2-hexyl, and 2-octyl dod 2-ethyl, 2-butyl, and 2-hexyl tetradecanols; 2-ethyl, 2-propyl, and 2-hexyl hexadecanols; 2-ethyl, 2-propyl, and 2-butyl octadecanols; 4-ethyl, 4-butyl, and 4-octyl dodecanols; 4-ethyl, 4-butyl, and 4-octyl tetradecanols; 4-ethyl, and 4-hexyl hexadecanol, and the like. The preferred compounds are branched chain alkyl alcohols with the 2-($C_2$–$C_8$ alkyl) such as, 2-octyldodecanol andd 2-hexyl dodecanol, alkanols being most suitable.

The composition, in addition to the above described components, must contain a fragrance emitting material. Most conventional fragrance materials are highly volatile essential oils. Even those which are less volatile contain highly volatile "top note" fractions which must be retained in the composition during processing to obtain the desired olfactory impact by the resultant molded article. In the instant invention any such conventional fragrance material, or combination thereof which has good clarity and compatability with the polyamide and alcohol of the present invention can be utilized. The fragrance material, may, for example, be a synthetically formed material or may be a naturally derived oil such as the oil of Bergamot, Bitter Orange, Caraway, Cedar Leaf, Cedar Wood, Champacc, Geranium, Lavender, Orange, Origanum, Patchouly, Pettitgrain, White Cedar and the like. The particular essential oil or combination of oils to be used depends upon the particular fragrance desired for emmission by the product formed.

As to the proportions, it is essential that the polyamide resin be present in an amount sufficient to form a self-supporting article which need be at least 40% by weight of the article to 60% by weight. The $C_{14}$–$C_{22}$ alkyl alcohol is present in amounts from about 35% to 55% by weight. The other essential component, the fragrance emitting material, is used in the amounts necessary to give the fragrance desired and normally should be from about 5 to 20% by weight.

The components can be processed with standard mixing and molding equipment, but such processing must be carried out at temperatures of from about 150° F to about 200° F. At these temperatures, the mixture of components is sufficiently fluid to achieve homogeneous mixing and molding, yet is capable of retaining the volatile materials contained therein. The mixture is cast into molds of any form, such as balls, bars, cylinders and the like. The resultant molded article, when cooled, is rigid, self-supporting, has a high degree of abrasion resistance, is stable, resists chipping, flaking, and the like, and permits the permeation of the desired fragrance into the atmosphere over a sustained period of time. The product can be readily used as a garment sachet without the problem of having the composition rub off onto the clothing to produce discoloration or an oily appearance thereon.

In addition to the essential ingredients described hereinabove, the fragrance releasing composition may contain conventional additives which are well known to those skilled in the art. These additives may include antioxidants, stabilizers, colorants, and the like. The necessity for any one or combination of the conventional additives can easily be determined and would depend upon the particular end use of the product.

Further, in order to facilitate the forming of a homogeneous mixture, light fraction mineral oil (sp. gr. at 25° C of 0.82 to 0.88) may be added to the composition during processing in amounts of up to about 15% by weight. The exact amount is determined by the particular alcohol and/or polyamide utilized. The addition of from about 5 to 12% is preferred and does not detract from the desired properties of the resultant product.

The pomander of the present invention may, in the alternative, be formed as a composite article having an inert core having thereabout the fragrance releasing composition described above. The term "inert" refers to a core containing no fragrance emitting material. The core, in such case, and the transparent polyamide fragrance composition of the present invention should be compatible with one another. The polyamide resin of the present invention is exceptionally suitable for a wide variety of core compositions in view of the fact that the polyamide resins will adhere to a wide variety of substances as is well known to those skilled in the art. The core may thus be formed from various polymeric substances, waxes, soap compositions, and the like. The core may be transparent or opaque, uncolored or colored, as will be dictated by the aesthetic appearance desired. Importantly, the core need not be rigid, since the instant composition after cooling is self-supporting and will retain the core in the shape desired.

The following examples are set forth for the purposes of illustration only and are not to be construed as a limitation of the present invention except as set forth in the appended claims. Parts and percentages are by weight unless otherwise indicated.

EXAMPLES I – III

Transparent sachets were formed from the compositions listed in Table I below:

TABLE I

| Component | I (parts) | II (Amount) | III |
|---|---|---|---|
| 2-octyldodecanol | 32.5 | 27.5 | 22.5 |
| Polyamide (condensate of dimeric linoleic acid and diethylene triamine) Versalon 1109 | 47 | 47 | 47 |
| 1,3 butylene glycol | 5 | 5 | 5 |
| Colorant | 0.0001 | 0.0001 | 0.0001 |
| Volatile Fragrance Oils (Spring Flower #754) (A volatile combination of oils commercially available from International Fragrance and Flavors Co.) | 5 | 10 | 15 |

The polyamide and alcohol were mixed in a conventional sigma blade mixer at 160° F. The fragrance material, glycol and colorant were added and mixed until uniformly dispersed. The mixture was heated to 170° F and cast into molds.

After cooling to room temperature, the molded articles were hard, did not show flaking, and were observed to emit the desired fragrance into the atmosphere over a several-month period. The compositions exhibited transparency, strength, dissolution, and entrapment of the volatile fragrance materials and the ability to be processed at moderate temperatures without loss of the fragrance material.

EXAMPLES IV – VI

Transparent sachets were formed from the same compositions and same manner as described in Example I, II and III except that 10 parts of mineral oil was added to each composition during the initial mixing of the polyamide and alcohol.

The cast compositions produced molded articles having the same properties as the articles of Examples I, II and III.

EXAMPLE VII

Compositions formed from the components of Examples I to VI described above were initially analyzed by standard analytical techniques against standards made with the same volatile fragrance material. Further, each composition was divided into separate samples which were heated at 190° F. for periods of 1, 3.5, and 7 hours, respectivley. The samples were allowed to cool and were analyzed for content of volatile fragrance material. All samples showed substantially no loss of said material.

EXAMPLE VIII

Two compositions were formed of the same materials, of the same amounts, and in the same manner as described in Example I above except that the amounts of polyamide used was altered to 57 parts and 42 parts respectively. The compositions were cast into molds of bar configuration. The resultant product, upon cooling to room temperature, exhibited transparency, strength, resistance to abrasion and was observed to emit the desired fragrance aroma over a period of several months.

EXAMPLE IX

Compositions are formed of the same components, of the same amounts, and in the manner as described in Example I hereinabove except that the alcohol, 2-octyl dodecanol, is substituted by 2-hexyl tetradecanol, and 2-butyl hexadecanol. The compositions are each cast at 180° C into bar molds. The resultant products exhibit the same properties observed with products formed from the composition of Example I.

EXAMPLE X

Compositions are formed of the same components, amounts and manner as described in Example I hereinabove except that Versalon 1109 is substituted by Versalon 1165, Versalon 1138 and Versalon 1130. These polyamide resins are similar to Versalon 1109 except for variations of molecular weights, and therefore, softening point. Each of the compositions produces a self-supporting, transparent molded sachet which exhibits resistance to chipping, and abrasion and exhibits a fragrance over a sustained period.

EXAMPLE XI

Compositions similar to Example I were formed using volatile fragrance oil combinations commercially available from Polak Frutal Works under I.D. numbers 8040664 and 8040674 and from International Fragrance and Flavors, Inc. under I.D. No. 401. The compositions form sustained release products similar to that described in Example I. Further, samples of each of the compositions are maintained in molden state at 190° F for 7 hours. Analysis of the samples shows substantially no loss of fragrance material.

EXAMPLE XII

A composite product was formed by initially forming a polymeric base inert core formed from 45 parts 2-octyldodecanol, 40 parts Versalon 1109, 10 parts mineral oil (light fraction) and 5 parts 1,3-butylene glycol. The components were mixed at 170° F until homogenous and cast into molds.

The formed cores were subjected to molten (170° F) fragrance composition formed from 32 parts 2-octyldodecanol, 47 parts Versalon 1109, 10 parts mineral oil (light fraction), 5 parts 1,3-butylene glycol, and 6 parts volatile fragrance material (Spring Flowers No. 754).

The composite product had a transparent appearance which was observed to emit a fragrance over a several-month period.

EXAMPLE XIII

In a similar manner to Example XII hereinabove, a composite fragrance emitting product was formed from an inert wax core formed by mixing 80 parts of parafin wax having a melting point of 145° F., 15 parts square wax (crystalline wax) having a melting point of 170°-175° F., and 0.03 parts of butylated hydroxy anisole. The core was formed by mixing the components at elevated temperature of 150° F. to obtain a substantially uniform mixture and then casting the resultant molten material into bars of desired size. The compositions of Examples I, II, and III described hereinabove, respectively, were molded about such solid bars to produce composite fragrance emitting products having an inert core and an outer layer of the composition which were observed to emit a fragrance over a sustained period of several months.

While the invention has been described in connection with preferred embodiments, it is not intended to limit the invention to the particular forms set forth, but on the contrary, it is intended to cover such alternatives, modifications, and equivalents as may be included within the spirit and scope of the invention as defined by the appended claims.

What is claimed is:

1. A shaped, self-supporting transparent article capable of emitting a fragrance over a sustained period comprising a substantially homogeneous mixture of from about 40 to 60% by weight of a polyamide resin formed from a polymerized fatty carboxylic acid and a polyamine, from about 35 to 55 percent by weight of a $C_{14}$-$C_{22}$ straight or branch chain alkyl alcohol and from about 5 to 20 percent by weight of a fragrance material.

2. The molded article of claim 1 wherein the polyamide has a softening point of less than about 200° C and a viscosity of less than about 90 poises at 225° C.

3. The molded article of claim 2 wherein the polyamide is formed from polymerized linoleic acid and a polyamine.

4. The method article of claim 2 wherein the $C_{14}$-$C_{22}$ alcohol is a 2-($C_2$-$C_8$ alkyl) alkanol.

5. The molded article of claim 4 wherein the alcohol is 2-octyldodecanol.

6. The article of claim 2 wherein the composition further contains up to 15 percent by weight of mineral oil.

7. A shaped self-supporting molded article capable of emitting a fragrance over a sustained period comprising an inert non-fragrance emitting core and, adhered thereto, a substantially homogeneous mixture comprising from about 40 to 60 percent by weight of a polyamide resin formed from a polymerized fatty carboxylic acid and a polyamine, from about 35 to 55 percent by weight of a $C_{14}$-$C_{22}$ alkyl alcohol and from about 5 to 20 percent by weight of a fragrance material.

8. The molded article of claim 7 wherein the inert core comprises a polyammide, wax or soap composition.

9. The molded article of claim 8 wherein the coating comprises a composition formed from about 40 to 60 percent by weight polyamide resin formed from polymerized linoleic acid and a polyamine, from about 35 to 55 percent 2-octyldodecanol and from about 5 to 20 percent of a volatile fragrance emitting material.

10. The molded article of claim 7 wherein the fragrance emitting mixture further contains up to 15% by weight of mineral oil.

11. A process of forming a self-supporting, shaped transparent article capable of emitting a fragrance over a sustained period comprising mixing at a temperature of from about 150° C. to 200° C. for a time to achieve a substantially complete homogeneous mixture from about 40 to 60 percent by weight of a polyamide resin formed from polymerized fatty carboxylic acid and a polyamine, from about 35 to 55 percent $C_{14}$-$C_{22}$ alkyl alcohol and from about 5 to 20 percent volatile fragrance material, casting the resultant molten mixture in a mold of desired configuration and cooling the molded article.

12. The process of claim 11 wherein the polyamide has a softening point of less than about 200° C. and a viscosity at 225° C. of less than 90 poises.

13. The process of claim 12 wherein the polyamide is formed from linoleic acid and a polyamine and the alcohol is a 2-($C_2$-$C_8$ alkyl) alkanol.

14. The process of claim 11 wherein the mixture further contains up to 15 percent of mineral oil.

15. A process of forming a self-supporting molded article capable of sustained fragrance emmission comprising initially forming a shaped article from a non-fragrance composition capable of bonding with a polyamide coating, adhereing about the shaped article a molten composition comprising a substantially homogeneous mixture of from about 40 to 60 percent by weight of a polyamide resin formed from a polymerized fatty carboxylic acid and a polyamine, from about 35 to 55 percent by weight of a $C_{14}-C_{22}$ alkyl alcohol, and from about 5 to 20 percent by weight of a fragrance material, and cooling said composition.

16. The process of claim 15 wherein the inert composition is a polyamide base composition; the coating composition comprises a polyamide formed from di- and trimeric linoleic acid and a polyamine and the alcohol is 2-octyldodecanol.

* * * * *

UNITED STATES PATENT AND TRADEMARK OFFICE
CERTIFICATE OF CORRECTION

PATENT NO. : 4,051,159

DATED : Sept. 27, 1977

INVENTOR(S) : Michael Tsoucalas, Kenneth W. Barclay & Jack M. Rogers

It is certified that error appears in the above-identified patent and that said Letters Patent are hereby corrected as shown below:

Col. 2, line 35, "dod" should be --dodecanols;--
Col. 2, line 42, after "($C_2$-$C_8$ alkyl)" insert --substituted--
Col. 2, line 42, "andd" should be --and--

Col. 4, line 47, "respectivley" should be --respectively--.
Col. 6, line 18 (Claim 4), "method" should be --molded--.
Col. 6, line 35 (Claim 8), "polyammide" should be --polyamide--.

Signed and Sealed this

Eighteenth Day of April 1978

[SEAL]

Attest:

RUTH C. MASON
Attesting Officer

LUTRELLE F. PARKER
Acting Commissioner of Patents and Trademarks